(12) United States Patent
Williams et al.

(10) Patent No.: US 9,931,086 B2
(45) Date of Patent: Apr. 3, 2018

(54) APPARATUS AND METHOD FOR BREAST IMMOBILIZATION

(71) Applicant: University of Virginia Patent Foundation, Charlottesville, VA (US)

(72) Inventors: Kelly Klanian Williams, Roswell, GA (US); Mark B. Williams, Earlysville, VA (US); Zongyi Gong, Charlottesville, VA (US); Tushita Patel, Charlottesville, VA (US); Emily M. Mastandrea, Madison, WI (US); Olivia P. Hamrah, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/375,879

(22) Filed: Dec. 12, 2016

(65) Prior Publication Data

US 2017/0215820 A1    Aug. 3, 2017

Related U.S. Application Data

(63) Continuation of application No. 14/434,587, filed as application No. PCT/US2013/064683 on Oct. 11, 2013, now Pat. No. 9,517,038.

(Continued)

(51) Int. Cl.
   *A61B 6/04*    (2006.01)
   *A61B 5/00*    (2006.01)
   *A61B 6/00*    (2006.01)

(52) U.S. Cl.
   CPC ......... *A61B 6/0414* (2013.01); *A61B 6/4258* (2013.01); *A61B 6/502* (2013.01)

(58) Field of Classification Search
   CPC .......... A61B 6/502; A61B 6/04; A61B 6/025; A61B 6/0414; A61B 6/4441; A61B 6/0457; A61B 5/4312; A61B 5/0091
   (Continued)

(56) References Cited

U.S. PATENT DOCUMENTS 3,971,950 A * 7/1976 Evans ................... A61B 6/502
                                                      378/180
4,212,306 A * 7/1980 Mahmud .............. A61B 5/0091
                                                      600/475

(Continued)

FOREIGN PATENT DOCUMENTS

WO   WO-2014059366 A1   4/2014

OTHER PUBLICATIONS

"U.S. Appl. No. 14/434,587, Notice of Allowance dated Aug. 5, 2016", 11 pgs.

(Continued)

*Primary Examiner* — David A Vanore
(74) *Attorney, Agent, or Firm* — Schwegman Lundberg & Woessner, P.A.

(57) ABSTRACT

This application discusses, among other things, curved plates for immobilizing a breast of a subject for medical imaging. In an example, an immobilization assembly Can include a curved compression plate assembly, a curved support plate assembly, an assembly coupling configured to position a first concave major surface of the curved compression plate assembly opposite a second concave major surface of the curved support plate assembly, wherein a cross section view through the curved compression assembly and the curved support plate assembly includes two portions of a single ellipse separated by a distance, and wherein the curved compression plate assembly and the curved support plate assembly are configured to immobilize (Continued)

the biological specimen between the first concave major surface and the second concave major surface.

20 Claims, 6 Drawing Sheets

Related U.S. Application Data

(60) Provisional application No. 61/713,196, filed on Oct. 12, 2012.

(58) Field of Classification Search
USPC .................................... 378/37, 208, 180, 20
See application file for complete search history.

(56) References Cited

U.S. PATENT DOCUMENTS

| | | | | |
|---|---|---|---|---|
| 4,926,453 | A | 5/1990 | Toniolo | |
| 4,943,986 | A * | 7/1990 | Barbarisi | A61B 6/502 |
| | | | | 378/208 |
| 5,029,193 | A * | 7/1991 | Saffer | A61B 6/502 |
| | | | | 378/180 |
| 5,595,177 | A | 1/1997 | Mena et al. | |
| 5,978,695 | A * | 11/1999 | Greenwald | G02B 21/34 |
| | | | | 600/407 |
| 6,574,499 | B1 * | 6/2003 | Dines | A61B 6/0414 |
| | | | | 128/915 |
| 6,833,703 | B2 * | 12/2004 | Sinkus | A61B 5/055 |
| | | | | 324/318 |
| 7,453,979 | B2 * | 11/2008 | Sendai | A61B 6/025 |
| | | | | 378/23 |
| 7,613,276 | B2 * | 11/2009 | Sendai | A61B 6/0414 |
| | | | | 378/37 |
| 8,155,421 | B2 * | 4/2012 | Ren | G06T 3/0006 |
| | | | | 382/128 |
| 8,532,253 | B2 * | 9/2013 | Virta | A61B 6/0457 |
| | | | | 378/37 |
| 9,020,094 | B2 * | 4/2015 | Popova | A61B 6/025 |
| | | | | 378/126 |
| 9,517,038 | B2 | 12/2016 | Williams et al. | |
| 2005/0265518 | A1 * | 12/2005 | Aubel | A61B 6/502 |
| | | | | 378/37 |
| 2006/0245541 | A1 * | 11/2006 | Aubel | A61B 6/502 |
| | | | | 378/37 |
| 2008/0112534 | A1 * | 5/2008 | Defreitas | A61B 6/0414 |
| | | | | 378/37 |
| 2009/0003519 | A1 | 1/2009 | Defreitas et al. | |
| 2009/0086891 | A1 * | 4/2009 | Ofuji | A61B 6/463 |
| | | | | 378/37 |
| 2012/0114095 | A1 * | 5/2012 | Smith | A61B 6/025 |
| | | | | 378/20 |
| 2012/0136234 | A1 | 5/2012 | Taku | |
| 2015/0282770 | A1 * | 10/2015 | Klanian | A61B 6/0414 |
| | | | | 378/208 |
| 2016/0081633 | A1 * | 3/2016 | Stango | A61B 6/0414 |
| | | | | 378/37 |

OTHER PUBLICATIONS

"U.S. Appl. No. 14/434,587, Preliminary Amendment filed Apr. 24, 2015", 6 pgs.

"International Application Serial No. PCT/US2013/064683, International Preliminary Report on Patentability dated Apr. 23, 2015", 8 pgs.

"International Application Serial No. PCT/US2013/064683, International Search Report dated Jan. 28, 2014", 2 pgs.

"International Application Serial No. PCT/US2013/064683, Written Opinion dated Jan. 28, 2014", 6 pgs.

* cited by examiner

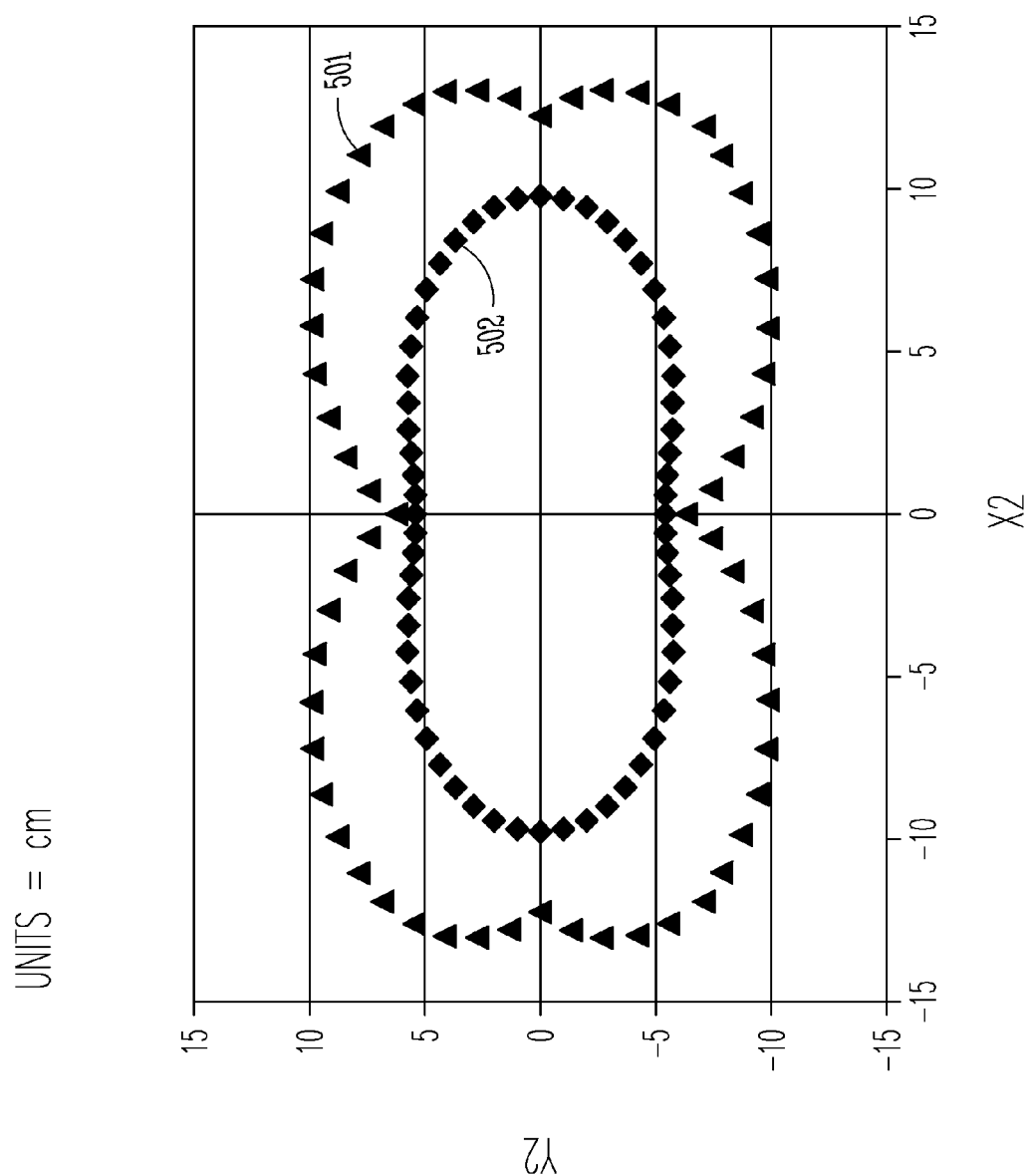

APPARATUS AND METHOD FOR BREAST IMMOBILIZATION

CLAIM OF PRIORITY

This patent application claims the benefit of priority to Klanian et al., U.S. Provisional Patent Application Ser. No. 61/713,196 entitled "BREAST IMMOBILIZATION DEVICE AND RELATED METHOD THEREOF," filed on Oct. 12, 2012, which is hereby incorporated by reference herein in its entirety.

BACKGROUND

At present, conventional x-ray mammography continues to be a gold standard for breast cancer screening. However, there has been growing interest in the use of other imaging modalities in conjunction with mammography in order to improve the sensitivity for detection of early malignancies and to reduce the false positive rates. Breast ultrasound (US) and contrast-enhanced magnetic resonance imaging (CE-MRI) are currently being used in this role, while other modalities including x-ray tomosynthesis, nuclear medicine, optical techniques, and acousto-optical techniques are under development. However, the type of breast support used in mammography, namely vigorous compression between two flat surfaces, is either incompatible with or suboptimal for the majority of these upcoming imaging modalities. As an example, the dual modality tomosynthesis (DMT) scanner, located at the University of Virginia Breast Care Center, performs both x-ray breast tomosynthesis (XBT) and molecular imaging breast tomosynthesis (MBIT) with the breast in a single configuration in order to assure that accurate co-registration can be obtained between the two resulting 3-D image sets. Both XBT and MBIT use a tomosynthesis image acquisition approach, in which multiple views of the breast are obtained over a range of viewing angles. XBT provides anatomical information and can reliably resolve objects on a sub-millimeter scale. MBIT provides functional information through the use of an intravenously injected tracer tagged with a radioisotope and has spatial resolution on the order of 2.5 to 5.0 mm. Preliminary human studies have demonstrated that the addition of MBIT to XBT can improve negative predictive value, specificity, and overall accuracy.

A significant issue in mammography can be obscuration of malignancies by superimposed normal breast tissue in the image. Superimposition is especially problematic for the estimated 40-60% of women whose breasts are categorized as radiodense. It is, in part, for this reason that in mammography the breast is flattened by compressing it between a flat breast support (usually the top surface of the detector assembly) and a flat compression paddle using a large (up to and potentially exceeding 40 pounds) compressive force. With regards to DMT scanning, the use of XBT reduces the ramifications of tissue overlap by generating 3-D images that can be viewed as thin slices, thereby substantially reducing the amount of clutter in each image slice compared to that in a mammographic image, which can sum all the healthy background tissue into one image.

Accordingly, there is a need for a new breast immobilization technique whose design is not constrained by the requirements of mammography and that could improve both image quality and patient comfort.

OVERVIEW

This application discusses, among other things, curved plates for immobilizing a breast of a subject for medical imaging. In an example, an immobilization assembly can include a curved compression plate assembly, a curved support plate assembly, an assembly coupling configured to position a first concave major surface of the curved compression plate assembly opposite a second concave major surface of the curved support plate assembly, wherein a cross section view through the curved compression assembly and the curved support plate assembly includes two portions of a single ellipse, and wherein the curved compression plate assembly and the curved support plate assembly are configured to immobilize the biological specimen between the first concave major surface and the second concave major surface.

This section is intended to provide an overview of subject matter of the present patent application. It is not intended to provide an exclusive or exhaustive explanation of the invention. The detailed description is included to provide further information about the present patent application

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5 illustrates graphically imaging transducer trajectories about an example breast immobilization device having curved compression and support plates and a breast immobilization device having flat compression and support plates.

DETAILED DESCRIPTION

The present inventors have recognized that current devices and methods for immobilizing certain portions of a patient's anatomy for medical imaging can be improved to help provide better quality medical images. In addition, such improvements can unexpectedly provide more patient comfort. In turn, more patient comfort can assist in even more improved imaging by allowing the device to comfortably immobilize the tissue of interest for longer imaging sessions.

As discussed above, new imaging modalities can provide three dimensional images of a biological specimen such as a subject's breast. Certain modalities can provide the three dimensional images without being adversely affected by the amount of mammographically dense tissue within the breast. The implication is that in some modalities, such as XBT, the compression force typically applied to a subject's breast can be greatly reduced, and the breast imaged in a more natural shape, without sacrificing the ability to detect small abnormalities (lesions). In MBIT, for example, a gamma camera can be used to visualize tracer distribution within the breast. To maximize MBIT spatial resolution, close proximity of the gamma camera to the breast is desired. The flat shape of existing mammographic breast immobilization devices forces the gamma camera to be placed at increasingly larger separation distances from the breast surface as the camera is positioned at various viewing angles away from the direction of compression. However, for both XBT and MBIT breast immobilization is important to assure that motion of the breast during image acquisition does not produce image blurring.

Figure 1A:
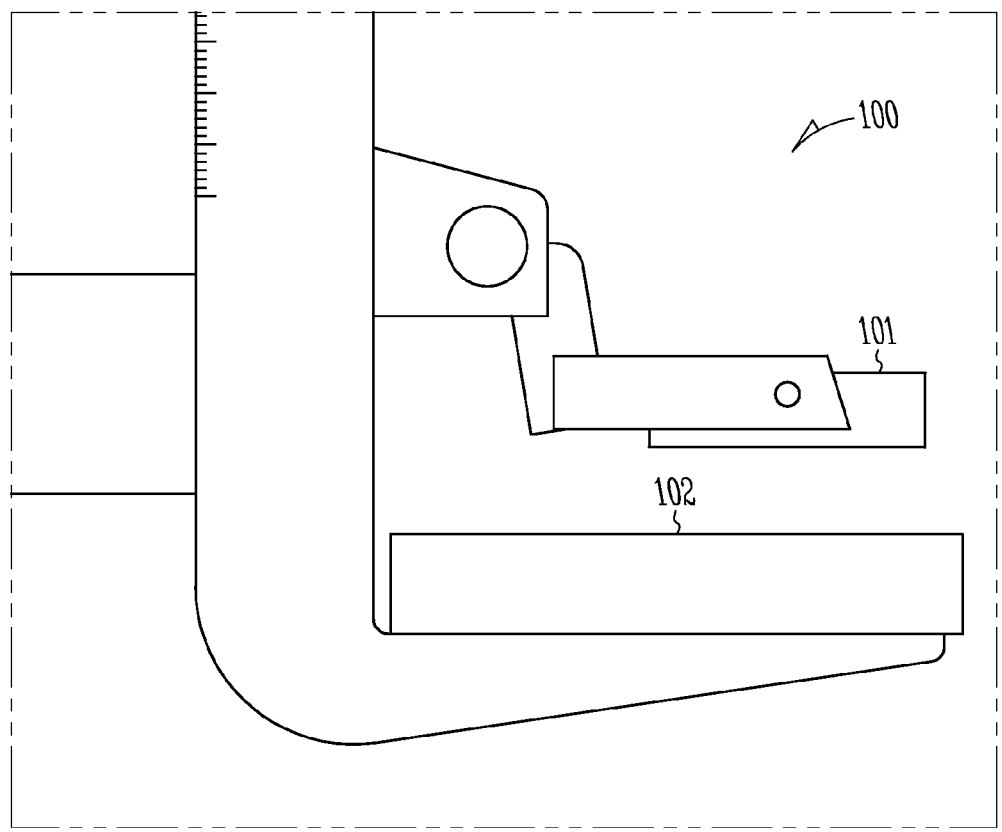
FIGS. 1A and 1B illustrate apparatus and effects of current breast immobilization devices.
Figure 1B:
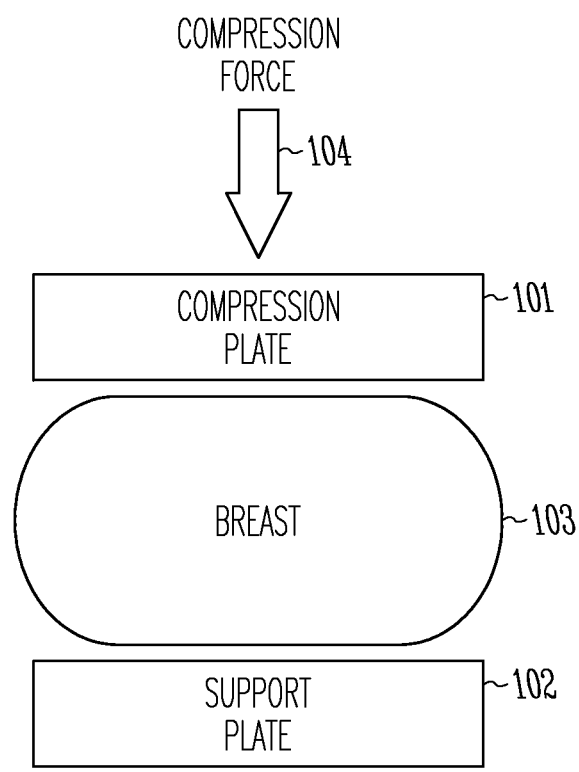

FIGS. 1A and 1B illustrate apparatus and effects of current breast immobilization devices. FIG. 1A illustrates a breast immobilization device having a flat, top compression paddle and a flat, bottom support panel 102. FIG. 1B illustrates the operation of the compression and support panels 101, 102 to flatten breast tissue 103 such that an x-ray mammography image can provide the detail necessary to evaluate whether a subject may have a lesion. The compression force 104 and resulting flattening of the breast tissue 103 can ameliorate superimposed, radio-dense, normal breast tissue from obscuring potential abnormalities in the final image. However, such compression can be extremely uncomfortable and may contribute to some patients avoiding opportunities to obtain a proper breast examination and diagnosis.

Figure 2:
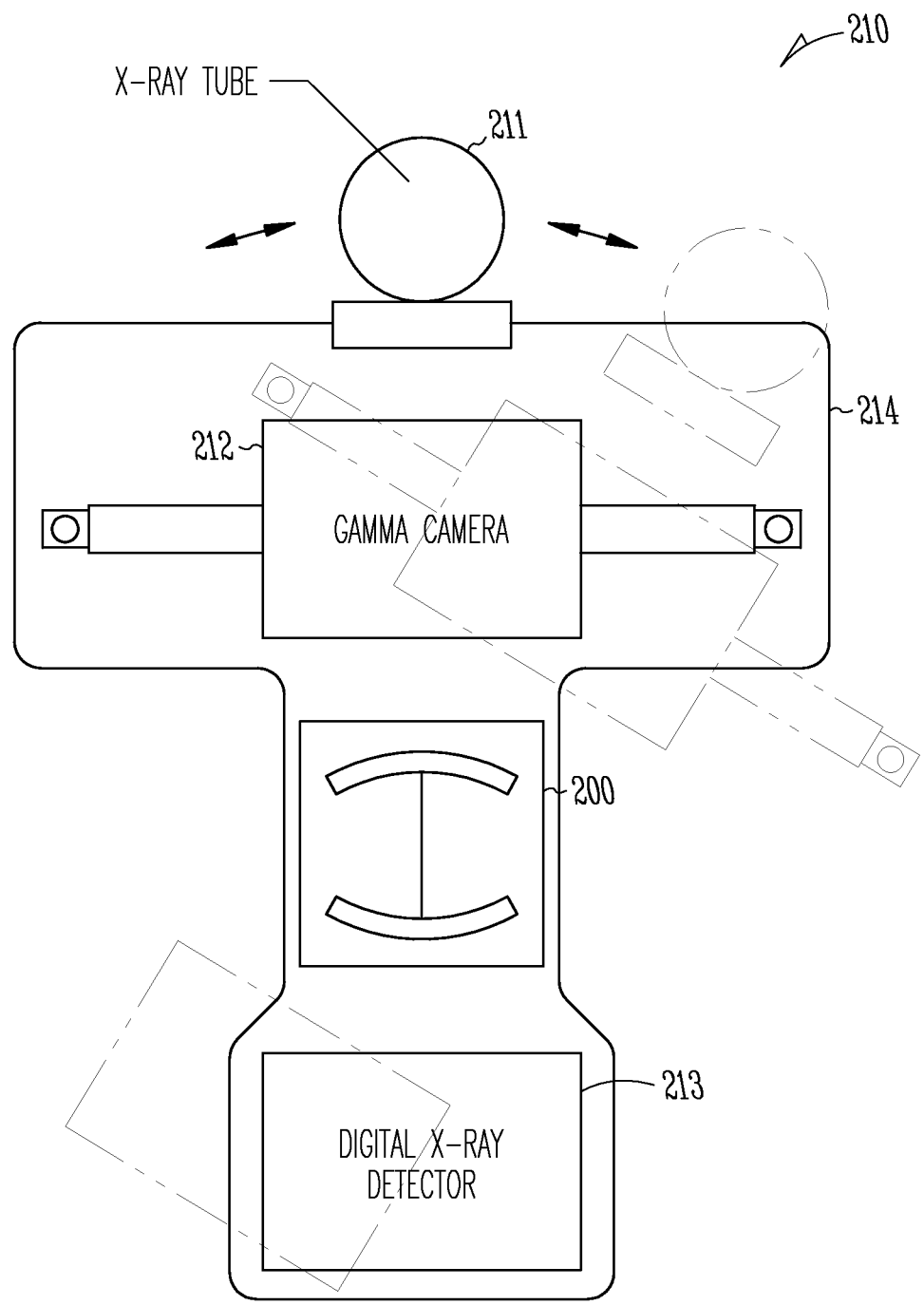
FIG. 2 illustrates a dual-modality scanner including an example breast immobilization device.

FIG. 2 illustrates a dual-modality scanner 210 including an example breast immobilization device 200. In certain examples, the dual-modality scanner 210 can include a number of imaging transducers 211, 212, 213, a rotatable scanner support structure 214, and the breast immobilization device 200. The imaging transducers 211, 212, 213 can be mounted to the rotatable scanner support structure 214. The rotatable scanner support structure 214 can rotate the imaging transducers 211, 212, 213 about a horizontal axis to allow the scanner transducers 211, 212, 213 to image a biological specimen (not shown). In certain examples, the imaging transducers 211, 212, 213 can be used to generate a number of projection images of the biological specimen using more than one imaging technique. During post-imaging processing, the projection images can be used to create a three dimensional image of the biological specimen and more particularly to create a three dimensional image of the internal structure of the biological specimen or of compounds within the specimen. Such images can be useful in finding abnormalities such as cancer, including but not limited to, breast cancer. In certain examples, the imaging transducers can include an x-ray tube 211, a x-ray detector 213, and a gamma camera 212. It is understood that other imaging transducers or combination of imaging transducers are possible without departing from the scope of the present subject matter.

In certain examples, the breast immobilization device 200 can be designed to allow a patient, such as a female patient, to stand or sit in front of a dual modality scanner 210 or other breast scanner and to have a breast imaged. The breast immobilization device 200 can immobilize the breast during the imaging process, which in certain circumstances can be lengthy. In addition, immobilization of the tissue of interest can allow certain details of the tissue structure to be reconstructed from the combination of different types of images generated using the scanner 210. Such biological structures can be more difficult to observe if the breast, or tissue of interest, is allowed to move or be repositioned between or during the imaging session. In certain examples, the improved shape and size of the breast immobilization device 200 can allow certain imaging transducers, such as the gamma camera 212, to be placed closer to the breast compared to standard mammographic immobilizers, and remain close to the breast as the scanner support structure 214 is rotated to image the breast from different imaging angles. In certain examples in which the support structure 214 does not rotate, the breast immobilization device 200 can be mounted to the scanner support structure 214 or a base structure (not shown). In some examples in which the support structure 214 rotates, the breast immobilization device 200 does not rotate with the scanner support structure 214 and can instead be mounted to a stationary base structure (not shown). In certain examples, one or more of the scanner transducers, such as the gamma camera 211, can be mounted to allow individual movement of the transducer with respect to other transducers mounted to the scanner support structure 214. Such mounting schemes can allow transducers to be placed out of the way while other transducers are used for scanning. In some examples, mounting schemes that allow a transducer to be moved independent of other transducers can allow the transducer to be placed in various positions or distances relative to the tissue of interest for certain desired imaging objectives.

Figure 3:
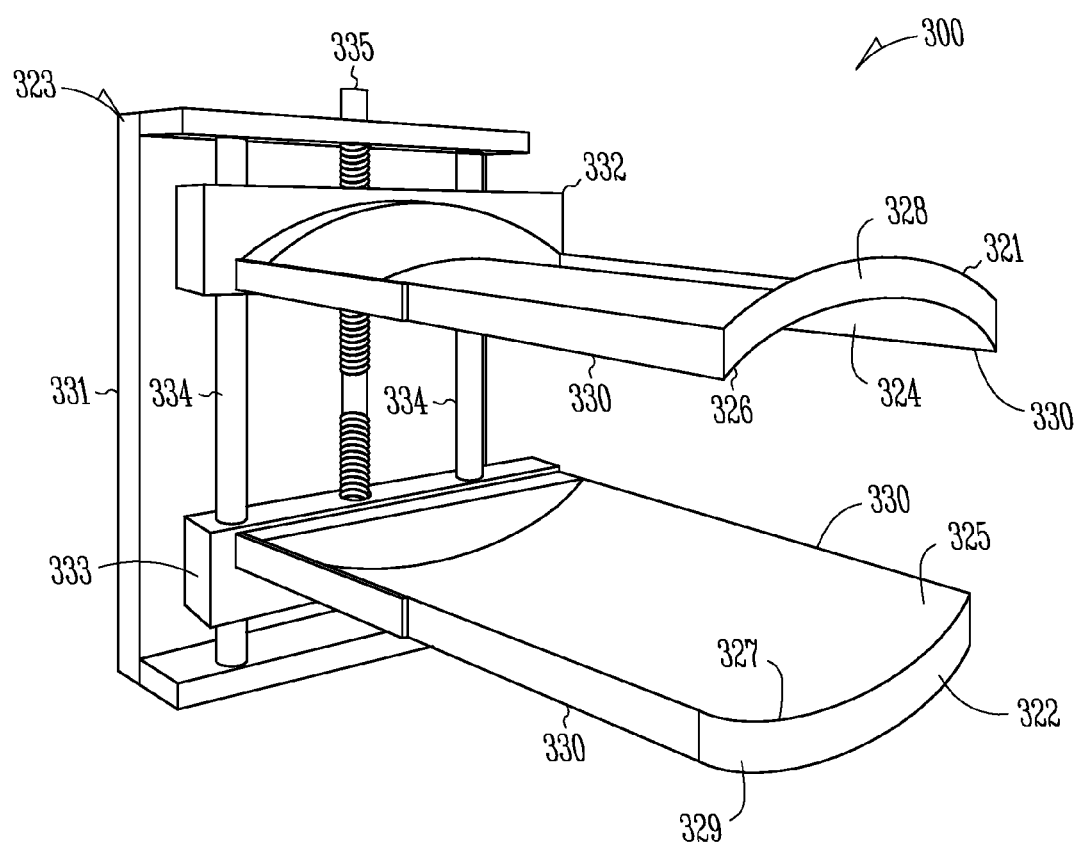
FIG. 3 illustrates generally an example breast immobilization device.

FIG. 3 illustrates generally an example breast immobilization device 300. In certain examples, the breast immobilization device 300 can include a curved compression plate 321, a curved support plate 322, and an integrated mounting and adjustment mechanism 323. In certain examples, the compression and support plates 321, 322 can include concave major surfaces 324, 325 configured to be mounted opposite each other and facing each other. In certain examples, a cross section of the plates 321, 322 as mounted to a scanner can resemble a truncated ellipse. The curved nature of the plates 321, 322 can allow a more comfortable experience for a patient during a breast imaging session. In addition, with certain imaging techniques some compression of the breast can be helpful, but significant compression is not necessary.

For multi-modal imaging, movement of the breast during the imaging process can significantly reduce the ability to reconstruct accurate images because the superimposed images can lose common reference landmarks that make accurate reconstruction possible. In certain examples, the curved compression and support plates 321, 322 can provide comfortable immobilization of the breast such that the multiple images modes can be executed without the breast tissue moving, even when those imaging intervals extend over several minutes.

In certain examples, a low attenuation material can be used to construct the curved compression and support plates 321, 322. Such materials can include, but are not limited to polycarbonate materials. In certain examples, a low attenuation material can allow accurate imaging when using x-rays with energies of approximately 25 keV. In certain examples, the truncated elliptical shape of the cross-section of the compression and support plates 321, 322 can provide significant physical access to the patient's breast or tissue even when the immobilization device is compressing the tissue. Such access can allow manipulation of the tissue for better imaging or can allow manipulation of the tissue for more patient comfort before the imaging session.

In certain examples, the leading curved edge 326, 327 of both the compression plate 321 and the support plate 322 can include a small lip whose height can be ½ inch or less. In some examples, the lip can include a radius at its intersection with the main body of the plate in order to provide a rounded surface at the breast surface. In some examples, the leading curved edges 326, 327 can be placed adjacent, such as immediately adjacent, the subject being imaged. For example, the leading curved edge 326 of the compression plate may be located just above the upper portion of the breast immediately adjacent the chest of the subject during an imaging session, and the leading curved edge 327 of the support plate may be located immediately adjacent the lower front rib cage area of the subject during the imaging session. In certain examples, the lips can stiffen the cantilevered ends of the compression plate 321 and the support plate 322. In addition to providing structural support for the cantilevered ends of the compression plate 321 and the support plate 322, the lip can provide a more comfortable transition of the front side of the plates 328, 329 and the curved major surfaces 324, 325 compared to a small radius transition without a lip.

In certain examples, the curved plates 321, 322 can be mounted to the integrated mounting and adjustment mechanism 323. In some examples, the integrated mounting and adjustment mechanism 323 can include a frame 331 for mounting the breast immobilization device 300 to the scanner. In certain examples, mounting brackets (not shown) can be used to mount the compression plate 321 and the support plate 322 to the integrated mounting and adjustment mechanism 323. In certain examples, a kit can include pairs of curved plates of varying size. Each pair of curved plates can include a compression plate and a support plate. The kit can be used to select a pair of plates that comfortably accommodate the size or shape of a breast of the subject.

In certain examples, the integrated mounting and adjustment mechanism 323 can include an adjustment system for moving the compression plate 321 and for moving the support plate 322. In some examples, the adjustment system can move the compression plate 321 and the support plate simultaneously 322. In certain examples, the adjustment system can include a first table 332 for coupling the compression plate 321 to the integrated mounting and adjustment mechanism 323. In an example, the adjustment system can include a second table 333 for coupling the support plate 322 to the integrated mounting and adjustment mechanism 323. In certain examples, the first table 332 and the second table 333 can move, or slide, along a first axis, such as a vertical axis, relative to the frame 331 of the integrated mounting and adjustment mechanism 323. In such examples, the first and second tables 332, 333 can be mounted to the frame 331 using a linear guide, such as but not limited to, linear ways, one or more rails 334 and one or more linear bearings integrated with the first and second tables 332, 333, or combinations thereof. In certain examples, the ways or the linear bearings of the motion system can ensure that the compression plate 321 and the support plate 322 remain aligned opposite each other over the full range of motion. In certain examples, the adjustment system can include a motion control mechanism to control the motion of the compression plate 321 or the motion of the support plate 322 along the axis of motion, such as a vertical axis of motion. In some examples, the motion control mechanism can include a lead screw 335 coupled to the frame 331 and one or more nuts coupled to the first table 332 and the second table 333.

In certain examples, the motion control mechanism can include a lead screw 335 coupled to the frame, a first nut coupled to the first table 332, and a second nut coupled to the second table 333. In some examples, the lead screw 335 can include a first lead thread for moving the first table 332 and a second lead thread for moving the second table 333. In some examples, turning the lead screw 335 in a first direction can simultaneously move first table 332 and the second table 333 toward each other such as for capturing and immobilizing a breast between the compression plate 321 and the support plate 322. Turning the lead screw in a second direction, opposite the first direction, can simultaneously move the first table 332 and the second table 333 away from each other along the axis of movement such as for releasing a breast from between the compression plate 321 and the support plate 322. In certain examples, the lead screw 335 can be coupled to a manual crank. In some examples, the lead screw 335 can be coupled to one or more gear boxes to locate the manual crank in a more accessible area. In some examples, the lead screw 335 can be driven with a motor. In some examples, the integrated mounting and adjustment mechanism 323 can include more than one screw, for example, to move the first and second tables 332, 333 independently.

Figure 4:
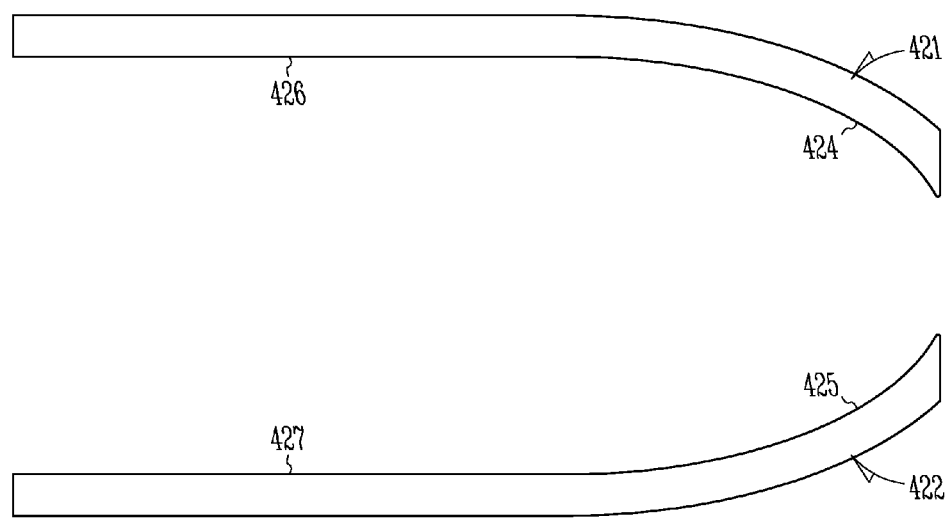
FIG. 4 illustrates generally a cross-section view of an example hybrid compression plate and an example hybrid support plate.

In certain imaging sessions, the upper outer quadrant of the patient's breast can be of particular interest for imaging as the location is frequently the site of abnormalities and is near lymph nodes of the patient. Clinical statistics show that the upper outer quadrant region of the patient's breast can account for a significant percentage of initial cancer detections. However, the region also includes pectoral muscle that without assistance can be difficult to keep immobile. FIG. 4 illustrates generally a cross-section view of an example hybrid compression plate 421 and an example hybrid support plate 422. In certain examples, the hybrid compression plate 421 and the support plate 422 can include a flat, or flattened, region 426, 427 that transitions from and is contiguous with an end of a concave major surface 424, 425 of each of the hybrid compression plate 421 and the hybrid support plate 422. In certain examples, the concave major surfaces 424, 425 include an elliptical shaped cross-section. The flattened region 426, 427 can define a horizontal plane perpendicular to the movement of the hybrid compression plate and the hybrid support plate when mounted to an adjustment mechanism such as that shown in FIG. 3. In certain examples, the flat regions 426, 427 can allow the immobilization device to capture at least a portion of the pectoral muscle and axillary tissue, and can assist in better and more comfortably immobilizing the pectoral muscle during the imaging session than without the flat regions 426, 427.

FIG. 5 illustrates graphically imaging transducer trajectories about an example breast immobilization device having curved compression and support plates and a breast immobilization device having flat compression and support plates. The graphic shows a first trajectory 501 about a breast immobilization device having flat compression and support plates, and a second trajectory 502 for an example breast immobilization device having curved compression and support plates. The graphic shows that the example immobilization device can allow certain imaging transducers to be closer to the tissue of interest at most if not all points within the imaging range of the scanner. In certain examples, the closer proximity of the imaging transducer can allow higher resolution images to be constructed. In some examples, the closer proximity of the scanner transducer to the breast can allow earlier detection of smaller abnormalities or lesions leading to earlier diagnosis and if necessary earlier intervention and treatment of the abnormalities or lesions. In certain situations, early detection and treatment of abnormalities can lead to improved chances for complete or significantly extended recovery from such abnormalities.

Additional Notes

In Example 1, an apparatus can include a scanner configured to image internal structure of a biological specimen of a subject, and an immobilization assembly configured to immobilize the specimen during an imaging session. The immobilization assembly can include a curved compression plate assembly having a first concave major surface, a curved support plate assembly having a second concave major surface, an assembly coupling configured to position the first concave major surface opposite the second concave major surface, wherein a cross section view through the curved compression plate assembly and the curved support plate assembly includes two portions of a single ellipse separated by a distance, and wherein the curved compression plate assembly and the curved support plate assembly are configured to immobilize the biological specimen between the first concave major surface and the second concave major surface.

In Example 2, the assembly coupling of Example 1 optionally includes a frame coupled to the scanner, and a linear guide coupled to the frame, the linear guide configured to align the first and second concave major surfaces, to allow motion of the first plate assembly and the second plate assembly along a linear axis, and to adjust the distance.

In Example 3, the linear guide of any one or more of Examples 1-2 optionally includes a linear rail.

In Example 4, each of the curved compression plate assembly and the curved support plate assembly of any one or more of Examples 1-3 optionally include a linear bearing configured to couple the curved compression plate assembly and the curved support plate assembly to the linear guide.

In Example 5, the apparatus of any one or more of Examples 1-4 optionally includes a motion control mechanism configured to simultaneously move the curved compression plate assembly and the curved support plate assembly along the linear axis.

In Example 6, the motion control mechanism of any one or more of Examples 1-5 optionally includes a lead screw.

In Example 7, the lead screw of any one or more of Examples 1-6 optionally includes a first lead thread configured to move the curved compression plate assembly, and a second lead thread configured to move the curved support plate assembly.

In Example 8, the lead screw of any one or more of Examples 1-7 optionally is configured to move the curved compression plate assembly and the curved support plate assembly toward each other along an axis of motion when the lead screw is turned in a first direction.

In Example 9, the lead screw of any one or more of Examples 1-8 optionally is configured to move the curved compression plate assembly and the curved support plate assembly away from each other along the axis of motion when the lead screw is turned in a second direction, the second direction opposite the first direction.

In Example 10, the curved compression plate of any one or more of Examples 1-9 optionally includes a curved edge and a side configured to be placed immediately adjacent the subject, the curved edge configured to transition between the first concave major surface of the curved compression plate and the side of the curved compression plate, and wherein the curved edge includes a lip with a radius, the lip configured to provide comfort to the subject and to stiffen the curved edge of the curved compression plate.

In Example 11, the curved support plate of any one or more of Examples 1-10 optionally includes a curved edge configured to be placed immediately adjacent the subject; the curved edge configured to transition between the second concave major surface of the curved support plate and a side of the curved support plate, and wherein the curved edge includes a lip with a radius, the lip configured to provide comfort to the subject and to stiffen the curved edge of the curved support plate.

In Example 12, the curved compression plate of any one or more of Examples 1-11 optionally includes a flat region contiguous with a portion of the first concave major surface, wherein the flat region is configured to immobilize pectoral muscle of the subject.

In Example 13, the curved support plate of any one or more of Examples 1-12 optionally includes a flat region contiguous with a portion of the second concave major surface, wherein the flat region is configured to immobilize pectoral muscle of the subject in conjunction with the flat region of the curved compression plate.

In Example 14, a method of immobilizing a breast of a subject for medical imaging can include placing the breast between a concave compression plate and a concave support plate, and moving the concave compression plate toward the concave support plate to capture the breast between the concave compression plate and the concave support plate.

In Example 15, the moving the concave compression plate of any one or more of Examples 1-14 optionally includes simultaneously moving the concave compression plate and the concave support plate toward each other to capture the breast between the concave compression plate and the concave support plate.

In Example 16, the method of any one or more of Examples 1-15 optionally includes capturing at least a portion of pectoral muscle of the subject between a first flat region contiguous with a concave major surface of the concave compression plate and a second flat region contiguous with a concave major surface of the concave support plate.

In Example 17, the moving the concave compression plate of any one or more of Examples 1-16 optionally includes sliding a table coupled to the concave compression plate along a vertical axis using a linear guide to capture the breast between the concave compression plate and the concave support plate.

In Example 18, the moving the concave compression plate of any one or more of Examples 1-17 optionally includes simultaneously sliding a second table coupled to the concave support plate along the vertical axis using the linear guide to capture the breast between the concave compression plate and the concave support plate.

In Example 19, the moving the concave compression plate of any one or more of Examples 1-18 optionally includes turning a lead screw to slide the first plate along the linear guide.

In Example 20, the moving the concave compression plate of any one or more of Examples 1-19 optionally includes turning a lead screw to simultaneously slide the first plate and the second plate along the linear guide.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of legal equivalents to which such claims are entitled.

What is claimed is:

1. An immobilization assembly configured to couple to a scanner and to immobilize a biological specimen during an imaging session of the scanner, the immobilization assembly comprising:
    a curved compression plate assembly having a first concave major surface;
    a curved support plate assembly having a second concave major surface;
    an assembly coupling configured to position the first concave major surface opposite the second concave major surface, wherein a cross section view through the curved compression plate assembly and the curved support plate assembly includes two portions of a single ellipse separated by a distance;
    a lead screw configured to simultaneously move the curved compression plate assembly and the curved support plate assembly along the linear axis; and
    wherein the curved compression plate assembly and the curved support plate assembly are configured to immobilize the biological specimen between the first concave major surface and the second concave major surface.

2. The immobilization assembly of claim 1, wherein the assembly coupling includes:
    a frame coupled to the scanner; and
    a linear guide coupled to the frame, the linear guide configured to align the first and second concave major surfaces, to allow motion of the first plate assembly and the second plate assembly along a linear axis, and to adjust the distance.

3. The immobilization assembly of claim 2, wherein the linear guide includes a linear rail.

4. The immobilization assembly of claim 3, wherein each of the curved compression plate assembly and the curved support plate assembly include a linear bearing configured to couple the curved compression plate assembly and the curved support plate assembly to the linear guide.

5. The immobilization assembly of claim 1, wherein the lead screw includes a first lead thread configured to move the curved compression plate assembly; and
    wherein the lead screw includes a second lead thread configured to move the curved support plate assembly.

6. The immobilization assembly of claim 5, wherein the lead screw is configured to move the curved compression plate assembly and the curved support plate assembly toward each other along an axis of motion when the lead screw is turned in a first direction.

7. The immobilization assembly of claim 6, wherein the lead screw is configured to move the curved compression plate assembly and the curved support plate assembly away from each other along the axis of motion when the lead screw is turned in a second direction, the second direction opposite the first direction.

8. The immobilization assembly of claim 1, wherein the curved compression plate includes a curved edge and a side configured to be placed immediately adjacent the subject, the curved edge configured to transition between the first concave major surface of the curved compression plate and the side of the curved compression plate; and
    wherein the curved edge includes a lip with a radius, the lip configured to provide comfort to the subject and to stiffen the curved edge of the curved compression plate.

9. The immobilization assembly of claim 1, wherein the curved support plate includes a curved edge configured to be placed immediately adjacent the subject;

the curved edge configured to transition between the second concave major surface of the curved support plate and a side of the curved support plate; and wherein the curved edge includes a lip with a radius, the lip configured to provide comfort to the subject and to stiffen the curved edge of the curved support plate.

10. The immobilization assembly of claim 1, wherein the curved compression plate includes a flat region contiguous with a portion of the first concave major surface, wherein the flat region is configured to immobilize pectoral muscle of the subject.

11. The immobilization assembly of claim 10, wherein the curved support plate includes a flat region contiguous with a portion of the second concave major surface, wherein the flat region is configured to immobilize pectoral muscle of the subject in conjunction with the flat region of the curved compression plate.

12. A method of immobilizing a breast of a subject for medical imaging, the method comprising:
placing the breast between a concave compression plate and a concave support plate; and
turning a lead screw in a first direction to simultaneously slide the concave compression plate and the concave support plate along a linear guide to capture the breast between the concave compression plate and the concave support plate, wherein the lead screw is configured to move the concave compression plate and the concave support plate toward each other along the linear guide when the lead screw is turned in the first direction.

13. The method of claim 12 wherein turning the lead screw in a first direction includes simultaneously moving the concave compression plate and the concave support plate toward each other to capture the breast between the concave compression plate and the concave support plate.

14. The method of claim 12, including capturing at least a portion of pectoral muscle of the subject between a first flat region contiguous with a concave major surface of the concave compression plate and a second flat region contiguous with a concave major surface of the concave support plate.

15. The method of claim 12, including turning the lead screw in a second direction to simultaneously slide the concave compression plate and the concave support plate away from each other along the linear guide to open a gap between the concave compression plate and the concave support plate.

16. The method of claim 15, wherein the lead screw includes a first lead thread configured to move the concave compression plate, and wherein the lead screw includes a second lead thread configured to move the concave support plate.

17. An system comprising:
a scanner configured to image internal structure of a biological specimen of a subject; and
an immobilization assembly configured to immobilize the specimen during an imaging session, wherein the immobilization assembly includes:
a curved compression plate assembly having a first concave major surface;
a curved support plate assembly having a second concave major surface;
an assembly coupling configured to position the first concave major surface opposite the second concave major surface, wherein a cross section view through the curved compression plate assembly and the curved support plate assembly includes two portions of a single ellipse separated by a distance;
a lead screw configured to simultaneously move the curved compression plate assembly and the curved support plate assembly along the linear axis; and
wherein the curved compression plate assembly and the curved support plate assembly are configured to immobilize the biological specimen between the first concave major surface and the second concave major surface.

18. The system assembly of claim 17, wherein the assembly coupling includes:
a frame coupled to the scanner; and
a linear rail coupled to the frame, the linear rail configured to align the first and second concave major surfaces, to allow motion of the first plate assembly and the second plate assembly along a linear axis, and to adjust the distance.

19. The system of claim 17, wherein the lead screw includes a first lead thread configured to move the curved compression plate assembly; and
wherein the lead screw includes a second lead thread configured to move the curved support plate assembly.

20. The system of claim 17, wherein the curved compression plate includes a first curved edge and a side configured to be placed immediately adjacent the subject, the first curved edge configured to transition between the first concave major surface of the curved compression plate and the side of the curved compression plate;
wherein the first curved edge includes a lip with a radius, the lip configured to provide comfort to the subject and to stiffen the first curved edge of the curved compression plate;
wherein the curved support plate includes a second curved edge configured to be placed immediately adjacent the subject, the second curved edge configured to transition between the second concave major surface of the curved support plate and a side of the curved support plate; and
wherein the second curved edge includes a lip with a radius, the lip configured to provide comfort to the subject and to stiffen the second curved edge of the curved support plate.

* * * * *